United States Patent [19]

Pilatte et al.

[11] Patent Number: 5,030,578
[45] Date of Patent: Jul. 9, 1991

[54] PROCESS FOR THE PURIFICATION OF C1-INHIBITOR

[75] Inventors: Yannick M. Pilatte, Rockville; Carl H. Hammer, Gaithersburg; Michael M. Frank, Bethesda; Louis F. Fries, Ellicott City, all of Md.

[73] Assignee: The United States of America as represented by the Secretary of the Department of Health and Human Services, Washington, D.C.

[21] Appl. No.: 377,334

[22] Filed: Jul. 10, 1989

[51] Int. Cl.$^5$ ............................................. G01N 30/100
[52] U.S. Cl. .......................................... 436/86; 435/2; 436/827; 436/821; 436/825; 436/174; 436/175; 436/178; 436/501; 436/63
[58] Field of Search ................. 435/2; 436/827, 821, 436/825, 174, 175, 178, 501, 63, 86

[56] References Cited

U.S. PATENT DOCUMENTS 4,642,284 2/1987 Cooper et al. .................... 436/512
4,960,712 10/1990 Theofilopoulous et al. ....... 436/501

OTHER PUBLICATIONS

Pillatte, Y. et al., J. of Immunological Methods, 120(1) 1989, 37–44, A Simplified Procedure for C1-Inh. Purification, A Novel Use for Jacalin-Agarose.

Primary Examiner—David L. Lacey
Assistant Examiner—Abanti B. Singla
Attorney, Agent, or Firm—Birch, Stewart, Kolasch & Birch

[57] ABSTRACT

C1-inhibitor (C1-Inh), the major regulatory protein of the classical pathway of complement activation, can be purified in a new, simplied three step procedure which includes PEG fractionation, jacalin-agarose chromatography and hydrophobic interaction chromatography on phenyl-Sepharose which takes advantage of the marked hydrophilicity of the inhibitor. This procedure has major advantages over those which have been the most frequently used. This method may be highly adaptable to bulk purification for clinical use cr for performing analytical or functional studies on genetically or pathologically altered C1-Inh from clinical specimens.

10 Claims, 6 Drawing Sheets

FIG. 2

PROCESS FOR THE PURIFICATION OF C1-INHIBITOR

BACKGROUND OF THE INVENTION

This invention relates to a method of purifying protein and more specifically, to a more expedient and direct method for purifying C1-inhibitor, inhibitor of the first component of human complement (hereafter called C1-Inh).

C1-Inh controls C1 activation by forming covalent complexes with activated C1r and C1s in a one-to-one stoichiometry (Harpel and Cooper 1795, Reboul et al, 1977). C1-Inh can also form complexes with other target enzymes and thereby is involved in the regulation of several other plasma proteolytic systems including the coagulation, fibrinolytic and contact systems (Cooper 1985). The gravity of the disease associated with C1-Inh deficiency (hereditary angioedema) demonstrates the physiological importance of this plasma protein (Davis 1988).

Recently a new type of acquired C1-Inh deficiency characterized by the presence of autoantibodies to the C1-Inh molecule and an abnormally low molecular weight form of the C1-Inh has been described by several groups (Jackson et al, 1986; Alsenz et al, 1987; Malbran et al, 1988). The autoantibodies do not seem to interfere with the initial cleavage of the inhibitor by the target enzymes but bind to the molecule in a way that prevents the irreversible inhibition of the enzymes (Malbran et al, 1988). The exact mechanism by which these antibodies inactivate the C1-Inh is unknown and in order to better understand this disease, it is necessary to provide highly pure and fully functionally active C1-Inh in order to conduct further studies. However, of the many methods published for the purification of C1-Inh (Haupt et al, 1970; Harpel and Cooper, 1975; Reboul et al, 1977; Nilsson and Wiman, 1982; Harrison, 1983; Prograis et al, 1987), all are time-consuming and some do not yield highly pure protein, part of the reason being that the chromatography material was not very selective.

Recently, Hiemstra and collaborators (1987), have reported that jacalin binds C1-Inh in serum and causes complement activation. Jack fruit (*Artocarous integrifolia*) lectin, also called jacalin, is a galactosyl-specific lectin (Krishna Sastry et al, 1988) which can be used to separate human IgA$_1$ from IgA$_2$ (Gregory et al, 1987; Skea et al, 1988). Jacalin appears to bind only a small number of human serum proteins (Roque-Barreira and Campos-Neto, 1985).

Prior art purification procedures include several time-consuming chromatographic steps in which it is necessary to identify the C1-Inh containing fractions from each chromatographic step by either immunochemical or functional assays. Finally, dialysis of the C1-Inh containing pools is required between each step. All known procedures are tedious and time-consuming.

SUMMARY OF THE INVENTION

C1-Inhibitor, the major regulatory protein of the classical pathway of complement activation, can be purified in a new, simplified three-step procedure which includes removal of interfering proteins ( by e.g. PEG fractionation), chromatography on jacalin-agarose and hydrophobic interaction chromatography on phenyl-Sepharose.

One aspect of the invention is based on the surprising finding that it is possible to isolate C1-Inh in purified form from blood plasma in a process which comprises the steps of:
(i) removal of interfering major serum proteins;
(ii) subjecting the purified material to chromatography on jacalin-agarose;
(iii) subjecting the C1-Inh-comprising eluate from (ii) to hydrophobic interaction chromatography;
(iv) isolating the eluate comprising the purified C1-Inh.

Hence, the process for the isolation of a purified form of C1-Inh, optionally in dried form, from blood plasma comprises the steps of:
(a) providing blood plasma samples;
(b) removal of interfering major serum proteins from said blood plasma samples to produce a purified plasma material essentially free from IgA;
(c) subjecting the purified material to chromatography on jacalin-agarose to produce an eluate containing the C1-Inh;
(d) subjecting said eluate containing C1-Inh to hydrophobic interaction chromatography to yield a first liquid phase containing the purified C1-Inh;
(e) transferring the C1-Inh from said first liquid phase to a second liquid phase, and;
(f) optionally isolating the C1-Inh in dry form.

Another aspect of the invention is related to a method for purifying and characterizing the low molecular weight forms of C1-Inh by utilizing the process as described above.

Still another aspect of the invention relates to a method for performing analytical and functional studies on genetically or pathologically altered C1-Inh from clinical specimens wherein blood plasma from patients suspected to suffer from diseases originating from altered C1-Inh conditions is subjected to a series of operations comprising the following steps:
(a) removal of interfering major serum proteins;
(b) subjecting the purified material to chromatography on jacalin-agarose;
(c) subjecting the C1-Inh-comprising eluate from (b) to hydrophobic interaction chromatography;
(d) isolating the eluate comprising the purified C1-Inh, and;
(e) subjecting the purified C1-Inh from step (d) to structural and functional studies by known methods.

Still another aspect of the invention is the method of use of the purified C1-Inh in the treatment of life-threatening swelling episodes which occur in patients with hereditary angioedema.

The purification procedure has three major advantages over those purification techniques which have been previously practiced.

Firstly, it includes only two chromatographic steps. Secondly, because the C1-Inh pool is cleanly and predictably separated from the unwanted proteins by differential elution conditions in both chromatographic steps, no antigenic or functional assays are required to define the desired peaks. Thirdly, only the final product is dialyzed while all previously practiced methods of purification require several buffer changes. Thus, the method of the present invention is much faster and simpler than previously published and practiced purification methods. About 10 to 12 mg of highly purified and fully active C1-Inh can be obtained within one day from 120 ml of plasma giving an average yield of 40-45%. This method may thus be highly adaptable to industrial bulk purification, for clinical use or for preparation of genetically or pathologically altered C1-Inh from clinical specimens. The novel method will, due to its simplicity and rapidity, allow purification of abnormal C1-Inh from patients suffering from hereditary or acquired angioedema and to perform analytical or functional studies on these abnormal molecules. Such studies which were impractical before because the previous methods were complicated and time-consuming, will ultimately lead to a better understanding of the biochemical defect underlying these diseases.

BRIEF DESCRIPTION OF DRAWINGS

FIG. 2: SDS-PAGE and Western blot analysis of the material eluted from the jacalin-agarose column.

DETAILED DESCRIPTION OF THE INVENTION

The first step in the purification process is to provide blood plasma samples (step (a)). This step is performed in a manner well known to persons skilled in the art.

It is especially important that step (b) comprises removal of the component IgA. This component, IgA, can be removed in a process which comprises fractionation by means of polyethylene glycol (PEG). PEG is used in a first fractionation step at a concentration which precipitates IgA and not C1-Inh. This first fractionation step is carried out by means of PEG at a concentration of 21.4% by weight. When IgA has been removed, the concentration of PEG is increased to a concentration which will precipitate the C1-Inh, i.e. at least 45% by weight. Removal of IgA by means of PEG fractionation as a first step is critical because jacalin-agarose, the first chromatographic resin, will preferentially bind IgA unless this protein is largely removed. The jacalin-agarose chromatography is highly selective because this lectin binds only a small number of human serum proteins (Roque-Barreira and Campos-Neto 1985). More than 99.8% of the protein in the starting material can be eliminated at this state and a 316-fold purification factor can be observed. (The other proteins eluted from the jacalin-agarose column have not been completely identified but it is unlikely that other complement components, especially C1r and C1s, are in this material (Roque-Barreira and Campos-Neto 1985). The chromatography on jacalin-agarose (step (c)), is carried out in a procedure which comprises rinsing with an aqueous solution and elution. The first washing (rinsing) of the jacalin-agarose is carried out wit phosphate buffered saline (PBS) containing EDTA and NPGB for the removal of non-C1-Inh, and thereafter, the second step comprises elution of the jacalin-agarose with melibiose in buffer for the elution of C1-Inh. The PEG fraction and the jacalin-agarose eluate can, however, contain serine protease activity as detected by chromogenic substrate assays. The inhibitor NPGB should therefore be included in all buffers to protect C1-Inh from unwanted degradation and/or complex formation.

Figure 4:
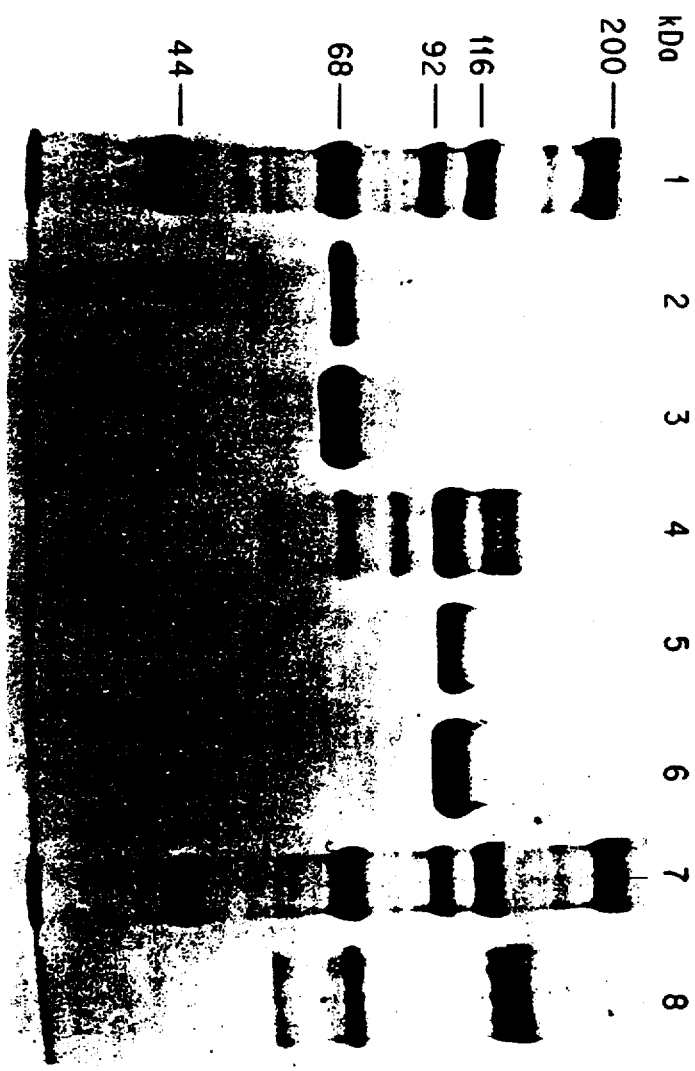
FIG. 4: SDS-PAGE analysis of the different steps of a typical purification.

The following step (step (d)) consists of hydrophobic interaction chromatography. This step is carried out on phenyl-Sepharose. This technique, which has been previously used for C1-Inh purification by Nilsson and Wiman (1982) but with a different resin (hexyl-Sepharose), takes advantage of the marked hydrophilicity of the inhibitor. In the conditions chosen, C1-Inh is the only protein which is not retained by the phenyl-Sepharose column. The purified product consists in a single chain protein with a molecular weight of about 105 kDa without an contaminating bands (FIG. 4).

When this step has been carried out, the C1-Inh is found in pure form solubilized in a buffer. If this buffer is of a type which will interfere with the intended use of the C1-Inh, it can be substituted with another liquid, which does not have any disadvantageous effect on the intended use of the pure C1-Inh.

As the next step (step (e)) of the process, the C1-Inh is, therefore, transferred into another liquid, i.e. PBS. This transfer may be performed by means of dialysis. If desired, the purified C1-Inh can then be isolated in dry form, e.g. by means of lyophilisation. C1-Inh is, however, stable and useful for the most purposes in solution in PBS.

Figure 6:
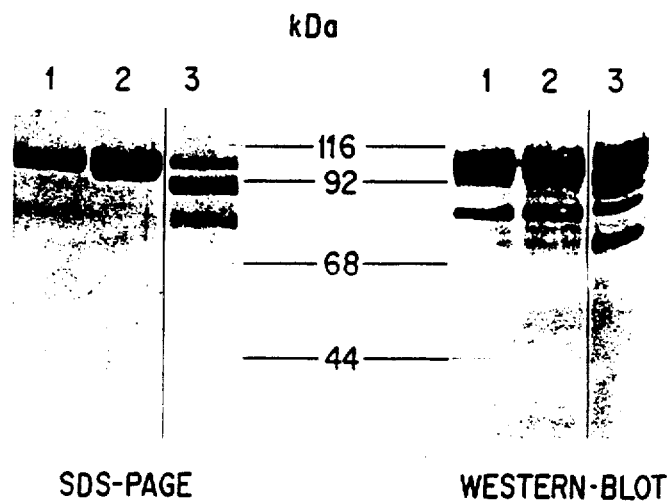
FIG. 6: SDS-PAGE and Western blot analysis of C1-Inh purified from three aged plasmas.

When plasmas have not been processed immediately after
collection, some degradation produces of C1-Inh were observed (FIG. 6). This observation suggests that this method could be valuable to purify and then characterize the low molecular weight forms of C1-Inh described in acquired C1-Inh deficiency.

The C1-Inh purified by this method is fully active, the specific activity measured by the inhibitor-enzyme complex immunoassay is constant throughout the purification (Table 1. (However, the purified protein had almost 4 times the specific activity of the C1-Inh present in the starting plasma when the L.I. assay is used. The reason of this discrepancy is unknown, but increase in specific activity during C1-Inh purification has been described by Reboul et al (1977) and Prograis and Associates (1987). In both papers, the authors suggested that a fraction of C1-Inh might have formed complexes giving rise to falsely low specific activities at early steps). However measured, retention of C1-Inh functional activity in material prepared according to the invention equals or exceeds that of all previous methods.

A special advantage of the process according to the invention is that it can be carried out unsupervised and automatically as there is no need for selecting specific fractions after the chromatographic steps.

Hence, the production can easily be scaled up to bulk preparation. Large available quantities of C1-Inh would provide possibilities for the preparation of solutions intended for use in the treatment of life-threatening swelling episodes which occur in patients with hereditary angioedema.

It is possible to characterize pathologically or genetically altered C1-Inh conditions in humans wherein a specimen of blood plasma from the patient is subjected to a procedure comprising the steps of:
(a) removal of interfering major serum proteins;
(b) subjecting the purified material to chromatography on jacalin-agarose;
(c) subjecting the C1-Inh comprising eluate from (b) to hydrophobic interaction chromatography;
(d) isolating the eluate comprising the purified C1-Inh, and (e) subjecting the purified C1-Inh to structural and functional analysis.

With this procedure, it will be possible to analyze abnormal C1-Inh from a large number of patients and thereby increase the knowledge and the structural basis of hereditary and acquired angioedema.

Abbreviations used throughout the specification are: C1-Inh, inhibitor of the first component of human complement; EDTA ethylenediamine tetraacetic acid; NPGB, p-nitrophenyl-p'-guanido-benzoate; PEG, polyethylene glycol; SDS, sodium dodecyl sulfate; Tris, tris(hydroxy-methyl)-amino methane.

The process according to the invention is further discussed below in the section "Materials and Methods".

MATERIALS AND METHODS

Antisera to purified proteins

Goat IgG anti-human IgA was obtained from Cappel Laboratories (Malvern, Penna.). Goat antiserum specific for human C1-Inh was prepared by injection of the highly purified protein prepared by the method of Prograis et al (1987) in Freund's complete adjuvant followed by repeated boosting with the antigen in incomplete adjuvant.

Assay procedures

C1-Inh functional level was measured by a minor modification of the conventional C1-inhibitor assay of Gigli et al (1968) and by using commercial C1-inhibitor-enzyme complex immunoassay kit (Cycotech, San Diego, Calif.) as described by the manufacturer. Briefly in the latter assay, samples to be tested were incubated with biotinylated activated C1s. Functionally active C1-Inh formed complexes with the exogenous C1s, after which incubation mixtures were transferred to microtiter wells coated with avidin which captured the biotinylated C1s-C1-Inh complexes. After washing, horseradish peroxidase-conjugated goat anti-human C1-Inh was added to each well. After incubation, a wash cycle removed excess conjugate and a chromogenic substrate was added. After incubation, the color intensity developed was measured spectrophotometrically at 405 nm and was proportional to the concentration of functional C$_{\overline{1}}$-Inh present in the test specimens.

SDS-Polyacrylamide gel electrophoresis (SDS-PAGE)

In order to examine their composition and purify, crude and purified protein preparations were electrophoresed on 7.5% polyacrylamide discontinuous mini slab gels by the method of Maizel et al (1971. The samples were run with high molecular weight markers (Bio-Rad Laboratories, Richmond, Calif.) in a Mini Protean TM II cell (Bio-Rad). The gels were stained for protein using Coomassie blue R-250 (Bio-Rad).

Immunoblotting

Electrophoretic transfer of proteins from SDS-PAGE slab gels to Immobilon PVDF transfer membrane (Millipore Corporation, Bedford, Mass.) was performed in a mini transblot cell (Bio-Rad) for 1 h on ice at 250 mA. Pre-stained molecular weight markers (Bio-Rad) were used to assess the transfer efficiency. The Immobilon PVDF transfer membrane was blocked overnight at room temperature with 5% (w/v) skim milk in 0.05M Tris, buffer pH 7.4, containing 0.15 M NaCl, 0.25 mM Thimerosal, 10 mM EDTA and 0.05% Tween 20 (SM-T$^3$EBS buffer) and then incubated with a saturating amount of goat anti-C1-Inh in SM-T$^3$EBS buffer at 37° C. for 2 hours. After washing with SM-T$^3$EBS buffer, the membrane was incubated with gold-labelled rabbit antibodies to goat IgG (Auroprobe BL plus RAG, Janssen Life Sciences Products, Piscataway, N.J.) for 2 h at 37° C., washed again and developed with the IntenSE BL kit (Janssen) as described by the manufacturer.

Radial immunodiffusion

Antigenic levels of C1-Inh And IgA were estimated by radial immunodiffusion according to Mancini et al (1965).

PREFERRED EMBODIMENT

The process according to the invention is illustrated in the following Example.

EXAMPLE

Plasma preparation

Blood from normal healthy volunteers was collected in plastic syringes containing a 20 x stock mixture (3 ml/60 ml of blood) of protease inhibitors: p-nitrophenyl-p'-guanido benzoate (NPGB Sigma Chemicals Co., St. Louis, Mo.), ethylene diamine tetraacetic acid (EDTA) and soybean trypsin inhibitor (SBTI) to achieve concentrations of 25 μM, 10 mM and 50 μM, respectively. Plasmas were obtained by centrifugation of the blood in polypropylene tubes. Approximately 120 ml of inhibitor-treated plasma were recovered from 240 ml blood. After this step all procedures were performed at 4° C. and polypropylene or polycarbonate containers were used to minimize the activation of the contact system proteins.

PEG fractionation

Because IgA is the major serum protein that binds immobilized Jacalin (Roque-Barreira et al, 1985), it was critical to determine the best conditions for the PEG fractionation in order to separate C1-Inh from the IgA. In preliminary experiments, it was established by radial immunodiffusion that almost all the IgA precipitated with 21.4% PEG while 75 to 90% of the highly soluble C1-Inh antigen was recovered in the 21.4 to 45% PEG precipitate. Inhibitor-treated plasma was brought to a final concentration of polytheylene glycol 3350 (PEG 3350; J.T. Baker Chemical Co., Phillipsburg, N.J.) of 21.4% (w/v). The solid powder was added to the plasma with constant stirring and allowed to equilibrate for 1 h. The precipitate was removed by centrifugation in a Sorvall RC2-B centrifuge at 10,000×g for 30 minutes. The supernatant was then adjusted to a final concentration of 45% PEG 3350 (w/v), equilibrated for 1 h and centrifuged to recover the precipitated proteins.

This procedure allowed almost complete resolution of C1-Inh from IgA.

Jacalin-agarose chromatography

The 45% PEG precipitate was solubilized in phosphate buffered isotonic saline (PBS) containing 10 mM EDTA and 25 μM NPGB and applied at 30 ml/h to a 1.5 cm diameter column containing 10 ml of Jacalin-agarose (Vector Laboratories, Burlingham, Calif.) equilibrated in the same buffer. Following application of the sample, the column was washed at the same flow rate with PBS containing 10 mM EDTA, 25 μM NPGB and 0.5 M NaCl until absorbance at 280 nm of the effluent approached zero. The column was then eluted with 0.125 M melibiose (Sigma Chemicals) in the same buffer.

Figure 1:
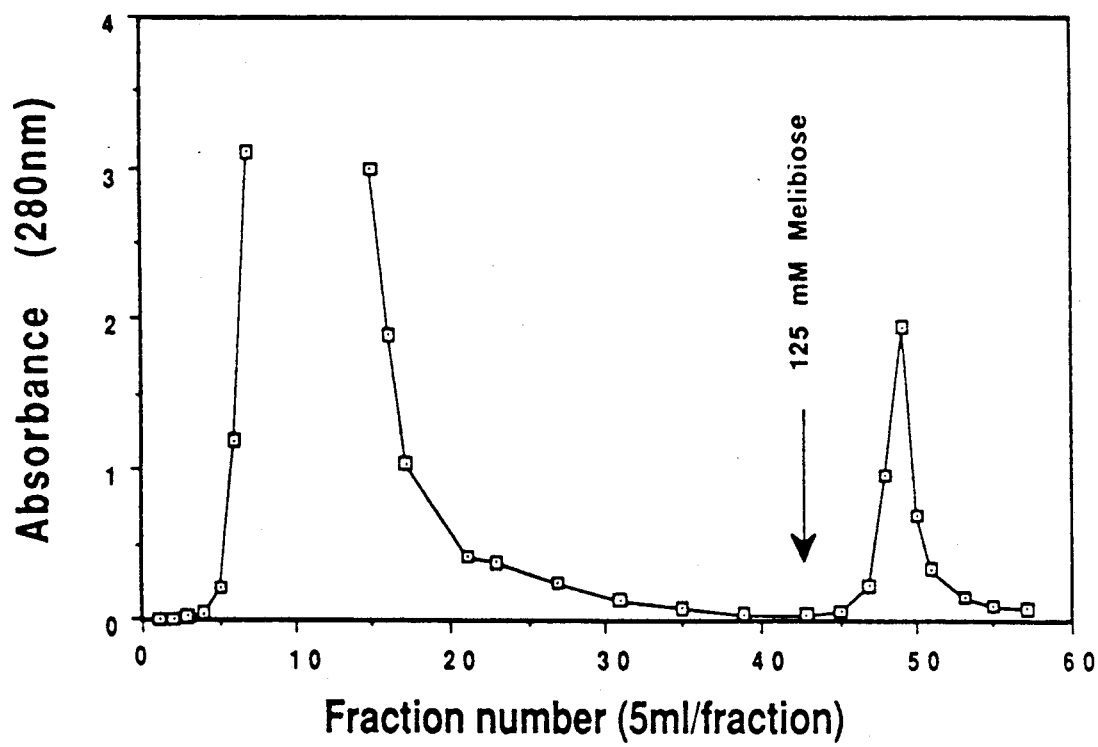
FIG. 1: Jacalin-agarose affinity chromatography.
Figure 2:
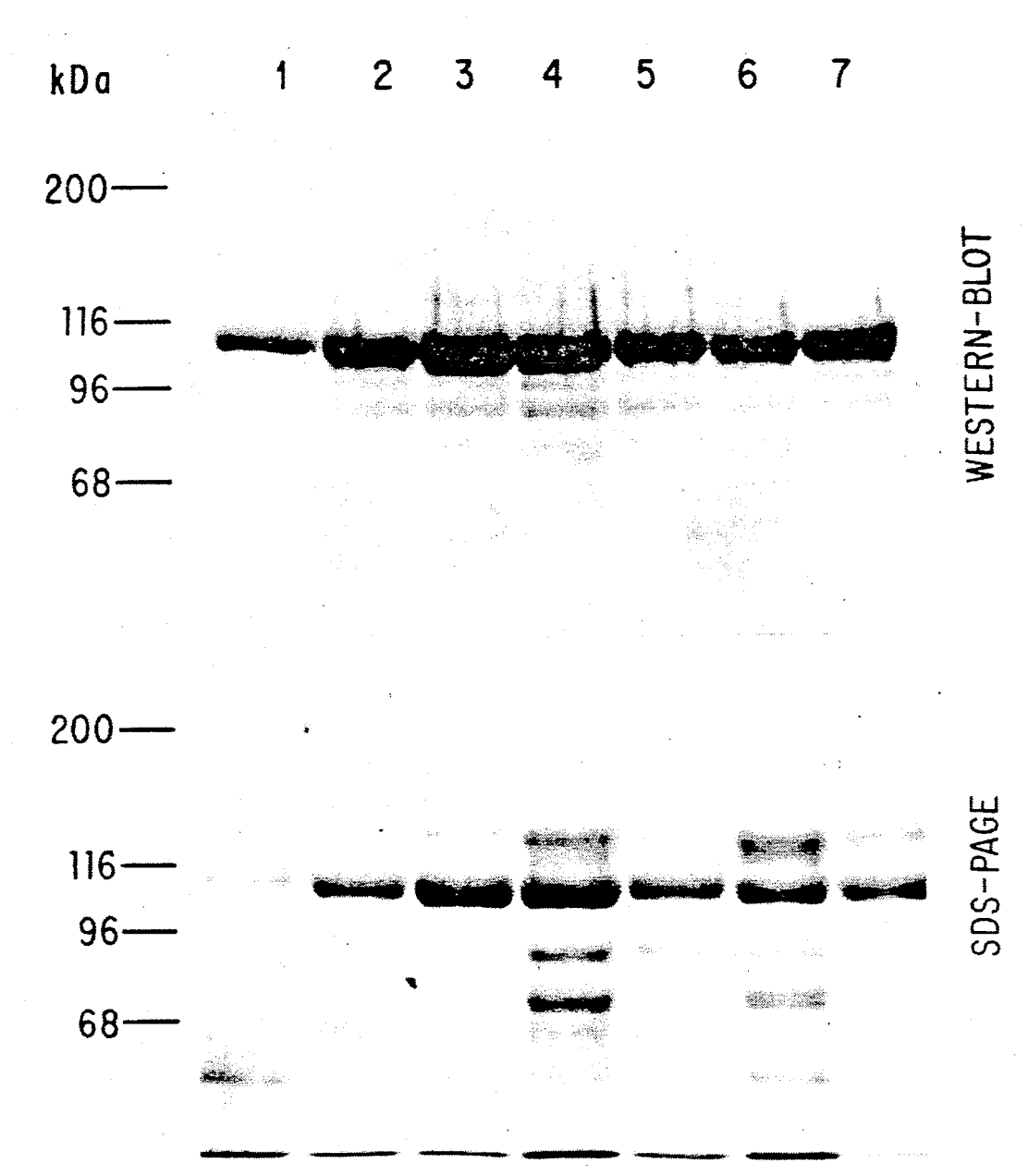

A typical profile depicted in FIG. 1, shows that the large majority of the proteins are not retained by the jacalin-agarose column. At this step 99.8% of the plasma proteins have been eliminated while the C1-Inh antigen recovery was more than 60% (Table 1). The presence in the buffer of a relatively high concentration of salt (0.5 M NaCl) is necessary because significant non-specific binding was observed with PBS in preliminary experiments. As expected this high salt buffer does not affect the jacalin binding capacity (Hagiwara et al, 1988). The jacalin binding material isolated from several plasmas has been subjected to SDS-PAGE. Interestingly, the protein pattern varied somewhat from one donor to another (FIG. 2): C1-Inh was identified in all the preparations by Western blot analysis (FIG. 2).

Phenyl-Sepharose Chromatography

Figure 3:
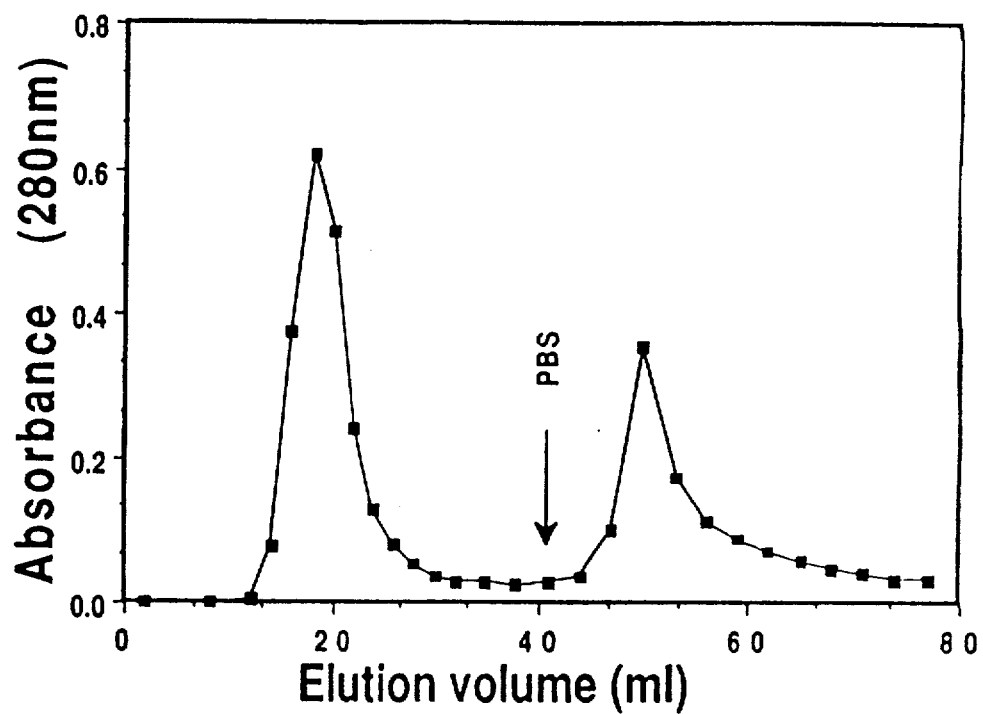
FIG. 3: Hydrophobic interaction chromatography of the jacalin-agarose eluate on a phenyl-Sepharose column.

The fractions containing the material specifically eluted from the jacalin-agarose column were pooled, concentrated under vacuum using 75 kDa exclusion collodion bags (Schleicher and Schuell, Keene, N.H.) and made 0.4M $(NH_4)_2SO_4$ by addition of an appropriate amount of a 4 M solution. The concentrated jacalin-agarose pool was then applied to a plastic column containing 7 ml of phenyl-Sepharose (Pharmacia Fine Chemicals, Piscataway, N.J.) equilibrated with PBS containing 0.4 M $(NH_4)_2SO_4$ and elution continued with 10 column volumes of the same buffer. Proteins were monitored at 280 nm and the peak corresponding to the material not retained by the column was pooled, concentrated to a final concentration of about 4 mg/ml and dialyzed against PBS. In some experiments the column was subsequently eluted with about 10 column volumes of PBS in order to recover part of the retained proteins. A typical chromatography profile is depicted in FIG. 3.

Figure 5:
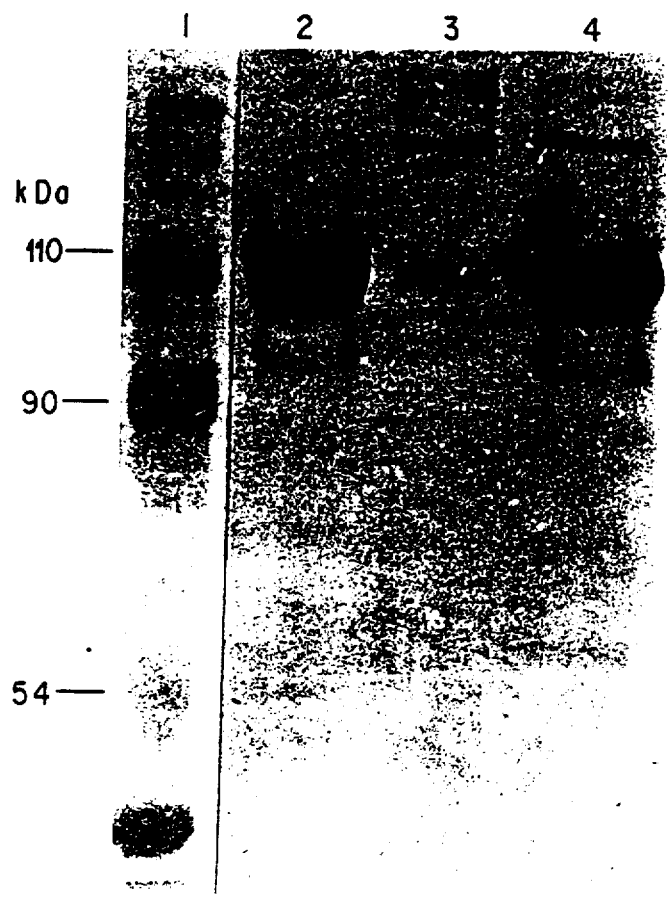
FIG. 5: Detection of high molecular weight C1-inhibitor-protease complexes by Western blot.

SDS-PAGE analysis of the material not retained by the phenyl-Sepharose column revealed a single band at 100–105 kDa identified as C1-Inh without any traces of contaminants (FIG. 4, lanes 5 and 6). Therefore this step allowed elimination of the remaining contaminating proteins, C1-Inh dropped through the column whereas the other proteins were retained. In some preparations, high molecular weight SDS-resistant complexes resulting presumably from the interactions of C1-Inh with proteases have been detected in the material applied to the phenyl-Sepharose column (FIG. 5, lane 4). However, these complexes were not detected in the purified C1-Inh (FIG. 5, lane 2) but in the fractions eluted from the column with PBS (FIG. 5, lane 3).

When PEG fractionation was not performed immediately after plasma collection, minor bands of lower molecular weight than C1-Inh were detected by SDS-PAGE in the purified material. Western blot analysis using goat anti-human C1-Inh revealed that these bands represented proteolytic degradation products of C1-Inh (FIG. 6).

C1-Inh functional activity

C1-Inh was assayed by a modification of the lysis inhibition (L.I.) method of Gigli et al (1968) and with the commercial Cytotech kit. In the latter method, the manufacturer suggests analysis of the results as a percentage of a normal standard plasma. However, because functional activity could not be readily followed this way, a normal plasma with a known C1-Inh titer measured by the Gigli assay was tested in parallel with the specimens and all the values obtained with the Cytotech kit were expressed pressed in "L.I. units". This calculation method was satisfactory since the titer of the plasma was $1.7 \times 10^7$ units/ml with the Cytotech method and $1.65 \times 10^7$ units/ml when measured directly by the L.I. assay (Table 1).

The specific activity measured by the commercial kit and expressed in L.I. units/µg C1-Inh antigen was fairly constant throughout the procedure and the final step represented a 778-fold purification (Table 1). When the L.I. assay was used, the specific activity increased 4-fold leading to a C1-Inh activity recovery of 150% while the antigen recovery was 39% and the purification factor was 3000 (Table 1).

TABLE 1

| | | | SUMMARY OF C1-INHIBITOR PURIFICATION | | | | | | |
|---|---|---|---|---|---|---|---|---|---|
| | Total protein ($A_{280}$) | Total C1-INH antigen (µg) | C1-INH activity (U × $10^{-7}$) | % Recovery | | | Specific activity | | |
| | | | | Total protein | C1-INH antigen | C1-INH activity | (U/µg) | (U/$A_{280}$) (×$10^{-3}$) | Fold Purification |
| Step 1 Plasma | 8870 | 31523 | 1.70 *1.65** | 100 | 100 | 100 *100** | 542.5 *523** | 1.93 *1.86** | 1 *1** |
| Step 2 21.4–45% PEG | 2398 | 29295 | 1.40 *3.10** | 27 | 92.3 | 82.5 *180** | 481.3 *1051** | 5.90 *12.9** | 3 *6.9** |
| Step 3 Jacalin-agarose | 17.2 | 19550 | 1.05 *2.80** | 0.2 | 62 | 61.4 *169** | 537.1 *1423** | 610 *1614** | 316 *868** |
| Step 4 Phenyl-Sepharose | 4.4 | 12250 | 0.66 *2.40** | 0.05 | 38.8 | 38.6 *147** | 538.8 *1975** | 1500 *5498** | 778 *2955** |

C1-INH functional activity was determined by inhibition of the C1 esterase hemolytic activity (numbers in italic*) and by using a commercial C1-Inhibitor-enzyme complex immunoassay kit. In both cases the C1-inhibitor is expressed in "lysis inhibition units" (see material and methods).

DETAILED DESCRIPTION OF THE DRAWINGS

FIG. 1: Jacalin-agarose affinity chromatography of the 21.4–45% PEG plasma precipitate solubilized in phosphate buffered isotonic saline (PBS) containing 10 mM EDTA and 25 µM NPGB and applied to a column containing 10 ml of Jacalin-agarose equilibrated in the same buffer. The column was washed with the same buffer containing 0.5 M NaCl until absorbance at 280 nm of the effluent approached zero. The column was then eluted with 0.125 M melibiose.

FIG. 2: SDS-PAGE and Western blot analysis of the material eluted from the jacalin-agarose column in 7 preparations from different individuals. Lower panel: proteins were stained with coomassie blue. Upper panel: proteins were transferred to Immobilon PVDF transfer membrane, incubated with a monospecific goat anti-human C1-Inh antiserum and developed with specific gold-labelled reagents.

FIG. 3: Hydrophobic interaction chromatography of the jacalin-agarose eluate on a phenyl-Sepharose column (10 ml) equilibrated in phosphate buffered isotonic saline (PBS) containing 0.4 M $(NH_4)_2SO_4$. Part of the absorbed proteins was eluted from the column with PBS.

FIG. 4: SDS-PAGE analysis (7.5%) of the different steps of a typical purification. Lane 1 and 7, molecular weight markers; lane 2, starting plasma; lane 3, 45% PEG precipitate; lane 4, Jacalin-agarose eluate; lanes 5 and 6, phenyl-Sepharose drop-through; lane 8, phenyl-Sepharose eluate. About 10 μg of each sample were applied except in lane 6 where 20 μg were loaded.

FIG. 5: Detection of high molecular weight C1-inhibitor-protease complexes by Western blot. Lane 1, molecular weight markers; lane 2, phenyl-Sepharose drop-through; lane 3, phenyl-Sepharose eluate; lane 4, Jacalin-agarose eluate. The membrane was handled as in FIG. 2.

FIG. 6: SDS-PAGE and Western blot analysis of C1-Inh purified from three aged plasmas.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A process for the isolation of a purified form of C1-inhibitor (C1-Inh), optionally in dried form, from blood plasma comprising the steps of:
   (a) obtaining blood plasma samples;
   (b) removing interfering major serum proteins from said blood plasma samples to produce a purified plasma material essentially free from IgA;
   (c) subjecting the purified material to chromatography on jacalin-agarose to produce an eluate containing the C1-Inh;
   (d) subjecting said eluate containing C1-Inh to hydrophobic interaction chromatography to yield a first liquid phase containing the purified C1-Inh;
   (e) transferring the C1-Inh from said first liquid phase to a second liquid phase, and
   (f) optionally isolating the C1-Inh in dry form.

2. A process according to claim 1 wherein the removal of IgA comprises fractionation by polyethylene glycol (PEG) precipitation.

3. A process according to claim 2, wherein the fractionation is carried out with PEG at a concentration which precipitates IgA and not C1-Inh.

4. A process according to claim 3, wherein the fractionation is carried out by PEG at a concentration of 21.4%.

5. A process according to claim 2, wherein the fractionation is carried out on two concentration levels of PEG.

6. A process according to claim 5, wherein the fractionation is carried out with PEG at a concentration of 21.4% and 45%, respectively.

7. A process according to claim 1, wherein the chromatography on jacalin-agarose is carried out with differential elution conditions.

8. A process according to claim 7, wherein said differential elution conditions comprises a first elution of the jacalin-agarose is carried out with phosphate buffered saline (PBS) containing EDTA and NPGB for the elution of non-C1-Inh material, and a second elution of the jacalin-agarose is carried out with melibiose in buffer for the elution of C1-Inh.

9. A process according to claim 1, wherein the hydrophobic interaction chromatography in step (d) is carried out on phenyl-Sepharose.

10. A process according to claim 1, wherein the transfer of the C1-Inh in step (e) is carried out by dialysis against PBS.

* * * * *

UNITED STATES PATENT AND TRADEMARK OFFICE
CERTIFICATE OF CORRECTION

PATENT NO. : 5,030,578
DATED : July 9, 1991
INVENTOR(S) : Yannick M. Pilatte, et al It is certified that error appears in the above-identified patent and that said Letters Patent is hereby corrected as shown below:

In the Drawings:

Insert figures 3 through 6, as shown on the attached pages.

Signed and Sealed this

Seventh Day of January, 1992

*Attest:*

HARRY F. MANBECK, JR.

*Attesting Officer*     *Commissioner of Patents and Trademarks*